(12) United States Patent
Burbank et al.

(10) Patent No.: US 7,404,821 B2
(45) Date of Patent: Jul. 29, 2008

(54) TREATMENT FOR POST PARTUM HEMORRHAGE

(75) Inventors: Fred H. Burbank, Laguna Niguel, CA (US); Michael L. Jones, San Clemente, CA (US); Jill Uyeno, Irvine, CA (US)

(73) Assignee: Vascular Control Systems, Inc., San Juan Capistrano, CA (US)

( * ) Notice: Subject to any disclaimer, the term of this patent is extended or adjusted under 35 U.S.C. 154(b) by 0 days.

(21) Appl. No.: 10/355,809

(22) Filed: Jan. 30, 2003

(65) Prior Publication Data
US 2004/0153097 A1 Aug. 5, 2004

(51) Int. Cl.
*A61B 17/00* (2006.01)
(52) U.S. Cl. ...................... 606/205; 606/119
(58) Field of Classification Search ............... 606/119, 606/205–208, 210, 211; 600/504, 424
See application file for complete search history.

(56) References Cited

U.S. PATENT DOCUMENTS

| | | | |
|---|---|---|---|
| 2,400,251 A | | 5/1946 | Nagel |
| 3,209,753 A | | 10/1965 | Hawkins et al. |
| 3,411,505 A | | 11/1968 | Nobis |
| 3,777,740 A | | 12/1973 | Hokanson |
| 3,779,248 A | * | 12/1973 | Karman ............ 606/207 |
| 4,120,302 A | * | 10/1978 | Ziegler ............ 606/207 |

(Continued)

FOREIGN PATENT DOCUMENTS

EP 0 890 342 A 1/1999

(Continued)

OTHER PUBLICATIONS

Anatomy of the Human Body. Gray, Henry. 1985. pp. 752, 1574 and 1575; included to show the anatomy of the part of the body Applicant's invention is directed to.*

(Continued)

*Primary Examiner*—Darwin P Erezo

(57) ABSTRACT

The invention is directed to instruments and procedures using such instruments for temporarily reducing or terminating blood flow through a female patient's uterine artery to treat post partum hemorrhage (PPH). The uterine artery is occluded by a clamping device which includes a pair of pivotally connected clamping members, with each of the clamping members having a handle and a clamping element at the distal end of the handle. The clamping elements are inclined with respect to the longitudinal axes of the handles at an included obtuse angle between about 120° and about 170°, preferably between about 130° and 160°. An artery locating sensor is provided on the distal end of at least one of the clamping elements. Preferably, the artery locating sensor is a Doppler ultrasound blood flow sensor. After birth, the clamping device is inserted into the female patient's post partum vaginal canal and advanced therein until one of the clamping elements Is in the patient's uterine cervix and the other clamping element is on the exterior of the uterine cervix. The clamping element on the exterior of the patient's uterine cervix is pressed against the patient's vaginal fornix and the clamping device closed so as to occlude the uterine artery disposed within tissue grasped by the clamping device. The clamping device is locked in the closed configuration and maintained in the condition until the patient's uterus is sufficiently clotted up to ensure termination of the hemorrhaging, typically about 5 minutes to about 7 hours.

11 Claims, 8 Drawing Sheets

U.S. PATENT DOCUMENTS

| | | | |
|---|---|---|---|
| 4,226,240 A * | 10/1980 | Walker, Jr. ................. | 606/207 |
| 4,292,960 A | 10/1981 | Paglione | |
| 4,428,374 A | 1/1984 | Auburn | |
| 4,428,379 A | 1/1984 | Robbins et al. | |
| 4,509,528 A | 4/1985 | Sahota | |
| 4,650,466 A | 3/1987 | Luther | |
| 4,757,823 A | 7/1988 | Hofmeister et al. | |
| 4,945,896 A | 8/1990 | Gade | |
| 4,991,588 A | 2/1991 | Pflueger et al. | |
| 4,994,069 A | 2/1991 | Ritchart et al. | |
| 5,037,430 A | 8/1991 | Hasson | |
| 5,037,433 A | 8/1991 | Wilk et al. | |
| 5,081,997 A | 1/1992 | Bosley, Jr. et al. | |
| 5,108,408 A | 4/1992 | Lally | |
| 5,201,314 A | 4/1993 | Bosley et al. | |
| 5,226,911 A | 7/1993 | Chee et al. | |
| 5,261,409 A | 11/1993 | Dardel | |
| 5,275,166 A | 1/1994 | Vaitenkunas et al. | |
| 5,289,831 A | 3/1994 | Bosley | |
| 5,336,229 A | 8/1994 | Noda | |
| 5,336,231 A | 8/1994 | Adair | |
| 5,383,922 A | 1/1995 | Zipes et al. | |
| 5,427,108 A | 6/1995 | Bollinger | |
| 5,456,693 A | 10/1995 | Conston et al. | |
| 5,458,596 A | 10/1995 | Lax et al. | |
| 5,488,958 A | 2/1996 | Topel et al. | |
| 5,496,331 A | 3/1996 | Xu et al. | |
| 5,507,744 A | 4/1996 | Tay et al. | |
| 5,542,944 A | 8/1996 | Bhatta | |
| 5,549,624 A | 8/1996 | Mirigian et al. | |
| 5,549,824 A | 8/1996 | Trumpf et al. | |
| 5,556,396 A | 9/1996 | Cohen et al. | |
| 5,562,680 A | 10/1996 | Hasson | |
| 5,570,692 A | 11/1996 | Morinaga | |
| 5,582,617 A | 12/1996 | Klieman et al. | |
| 5,588,960 A | 12/1996 | Edwards et al. | |
| 5,591,173 A | 1/1997 | Schifano | |
| 5,598,841 A | 2/1997 | Taniji et al. | |
| 5,614,204 A | 3/1997 | Cochrum | |
| 5,658,299 A | 8/1997 | Hart | |
| 5,662,676 A | 9/1997 | Koninckx | |
| 5,662,680 A | 9/1997 | Desai | |
| 5,665,096 A | 9/1997 | Yoon | |
| 5,672,153 A | 9/1997 | Lax et al. | |
| 5,672,172 A | 9/1997 | Zupkas | |
| 5,674,243 A * | 10/1997 | Hale ......................... | 606/205 |
| 5,691,314 A | 11/1997 | Hodgen | |
| 5,697,937 A | 12/1997 | Toma | |
| 5,697,942 A | 12/1997 | Palti | |
| 5,702,407 A | 12/1997 | Kaji | |
| 5,713,371 A | 2/1998 | Sherman et al. | |
| 5,713,896 A | 2/1998 | Nardella | |
| 5,713,942 A | 2/1998 | Stern et al. | |
| 5,715,832 A | 2/1998 | Koblish et al. | |
| 5,716,389 A | 2/1998 | Walinsky et al. | |
| 5,720,743 A | 2/1998 | Bischof et al. | |
| 5,749,879 A | 5/1998 | Middleman et al. | |
| 5,759,154 A | 6/1998 | Hoyns | |
| 5,766,135 A | 6/1998 | Terwilliger | |
| 5,776,129 A | 7/1998 | Mersch | |
| 5,792,059 A | 8/1998 | Furia et al. | |
| 5,797,397 A | 8/1998 | Rosenberg | |
| 5,800,378 A | 9/1998 | Edwards et al. | |
| 5,817,022 A | 10/1998 | Vesely | |
| 5,836,906 A | 11/1998 | Edwards | |
| 5,840,033 A | 11/1998 | Takeuchi | |
| 5,895,386 A | 4/1999 | Odell et al. | |
| 5,895,395 A | 4/1999 | Yeung | |
| 5,899,861 A | 5/1999 | Friemel et al. | |
| 5,904,651 A | 5/1999 | Swanson et al. | |
| 5,910,484 A | 6/1999 | Haupert, Jr. | |
| 5,911,691 A | 6/1999 | Mochizuki et al. | |
| 5,916,173 A | 6/1999 | Kirsner | |
| 5,921,933 A | 7/1999 | Sarkis et al. | |
| 5,922,008 A * | 7/1999 | Gimpelson ................. | 606/207 |
| 5,941,889 A | 8/1999 | Cermak | |
| 5,979,453 A | 11/1999 | Savage et al. | |
| 6,013,088 A | 1/2000 | Karavidas | |
| 6,015,541 A | 1/2000 | Greff et al. | |
| 6,019,724 A | 2/2000 | Gronningsaeter et al. | |
| 6,032,673 A | 3/2000 | Savage et al. | |
| 6,033,398 A | 3/2000 | Farley et al. | |
| 6,034,477 A | 3/2000 | Peeters et al. | |
| 6,035,238 A | 3/2000 | Ingle et al. | |
| 6,039,693 A | 3/2000 | Seward et al. | |
| 6,045,508 A | 4/2000 | Hossack et al. | |
| 6,066,139 A | 5/2000 | Ryan et al. | |
| 6,077,257 A | 6/2000 | Edwards et al. | |
| 6,080,118 A | 6/2000 | Blythe | |
| 6,096,051 A | 8/2000 | Kortenbach et al. | |
| 6,106,473 A | 8/2000 | Violante et al. | |
| 6,152,874 A | 11/2000 | Looney et al. | |
| 6,169,914 B1 | 1/2001 | Hovland et al. | |
| 6,175,751 B1 | 1/2001 | Maizes | |
| 6,186,947 B1 | 2/2001 | Ouchi | |
| 6,210,330 B1 | 4/2001 | Tepper | |
| 6,231,515 B1 | 5/2001 | Moore et al. | |
| 6,254,601 B1 | 7/2001 | Burbank et al. | |
| 6,261,234 B1 | 7/2001 | Lin | |
| 6,280,441 B1 | 8/2001 | Ryan | |
| 6,293,954 B1 * | 9/2001 | Fogarty et al. ............. | 606/151 |
| 6,299,621 B1 | 10/2001 | Fogarty et al. | |
| 6,368,340 B2 | 4/2002 | Malecki et al. | |
| 6,371,973 B1 | 4/2002 | Tepper | |
| 6,425,867 B1 | 7/2002 | Vaezy et al. | |
| 6,602,251 B2 | 8/2003 | Burbank et al. | |
| 6,610,074 B2 | 8/2003 | Santilli | |
| 6,905,506 B2 * | 6/2005 | Burbank et al. ............ | 606/205 |
| 2002/0111537 A1 | 8/2002 | Taylor et al. | |
| 2002/0165579 A1 | 11/2002 | Burbank et al. | |
| 2002/0183771 A1 | 12/2002 | Altieri et al. | |
| 2002/0188306 A1 * | 12/2002 | Burbank et al. ............ | 606/151 |
| 2003/0018270 A1 | 1/2003 | Makin et al. | |
| 2003/0120306 A1 * | 6/2003 | Burbank et al. ............ | 606/205 |

FOREIGN PATENT DOCUMENTS

| | | |
|---|---|---|
| GB | 2 302 025 A | 1/1997 |
| WO | WO 99/11179 A | 3/1999 |
| WO | WO 01/68720 | 9/2001 |
| WO | WO 01/80713 | 11/2001 |
| WO | WO 02/00192 | 1/2002 |
| WO | WO 02/078521 | 10/2002 |

OTHER PUBLICATIONS

International Search Report for PCT/US03/35815 mailed Jun. 30, 2004.

International Search Report for PCT/US04/01949, mailed Nov. 23, 2004.

International Search Report for PCT/US04/03023 mailed Feb. 9, 2005.

International Search Report for PCT/US2004/038276, mailed Mar. 15, 2005.

International Preliminary Report of Patentability for Serial No. PCT/US04/01935, mailed Jul. 8, 2005.

* cited by examiner

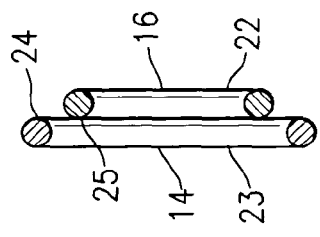
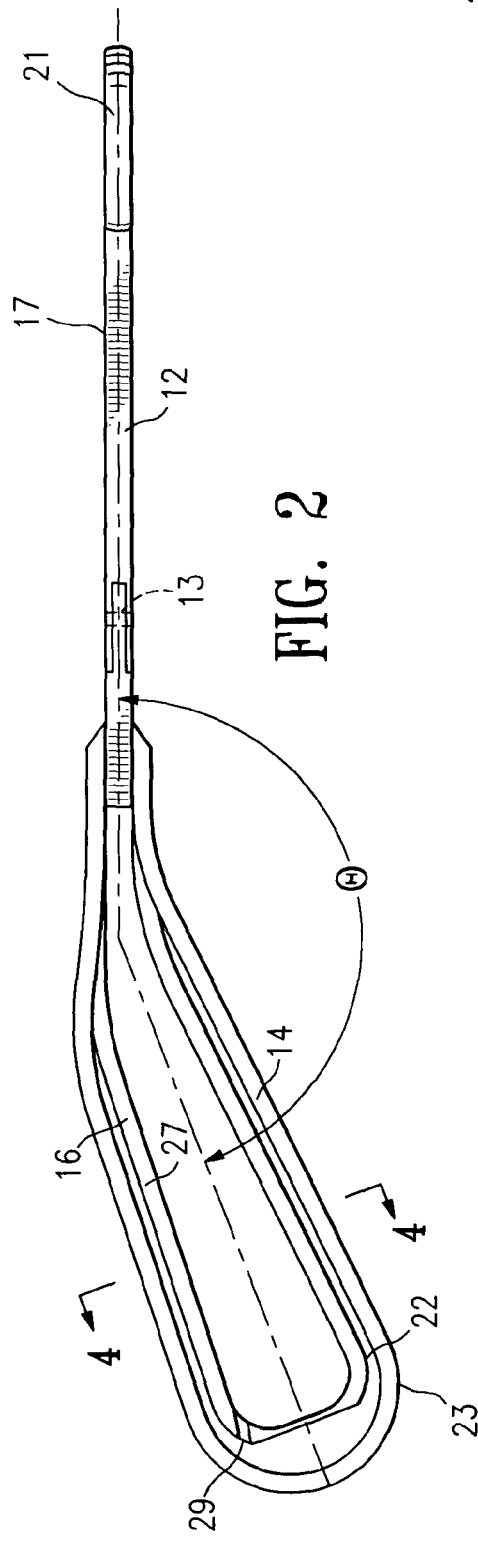
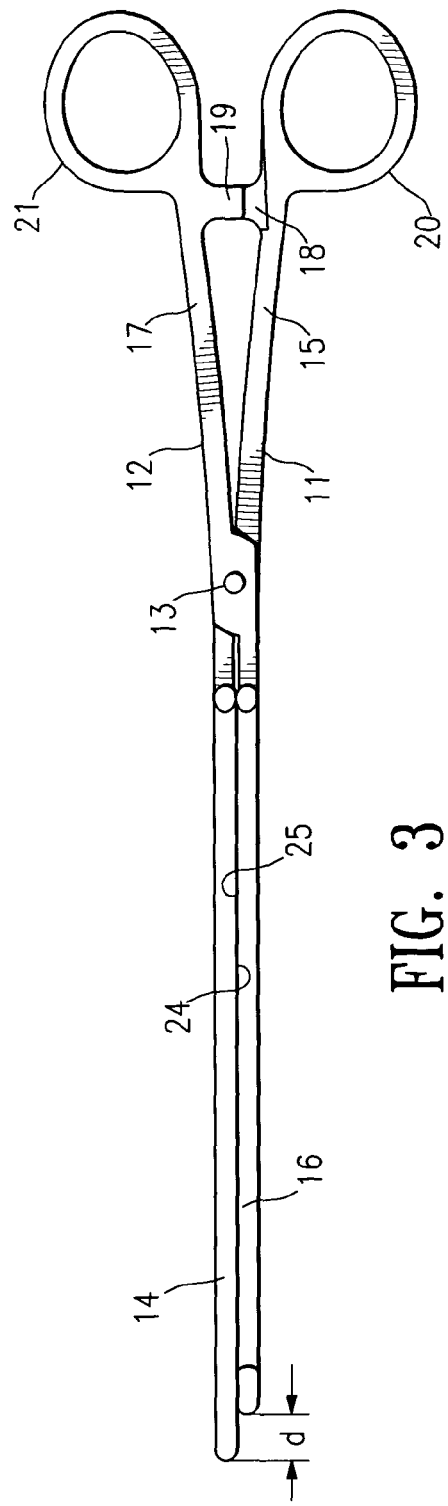

4 HOURS POST-PARTUM SAGGITAL VIEW

JUST PREGNANT SAGGITAL VIEW

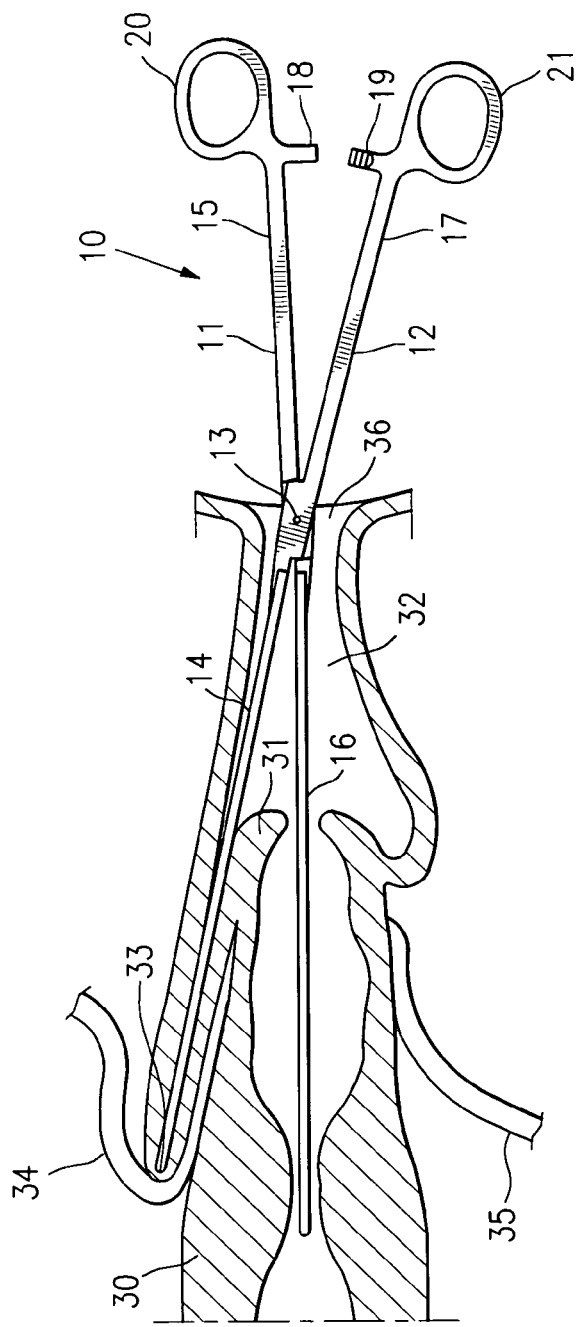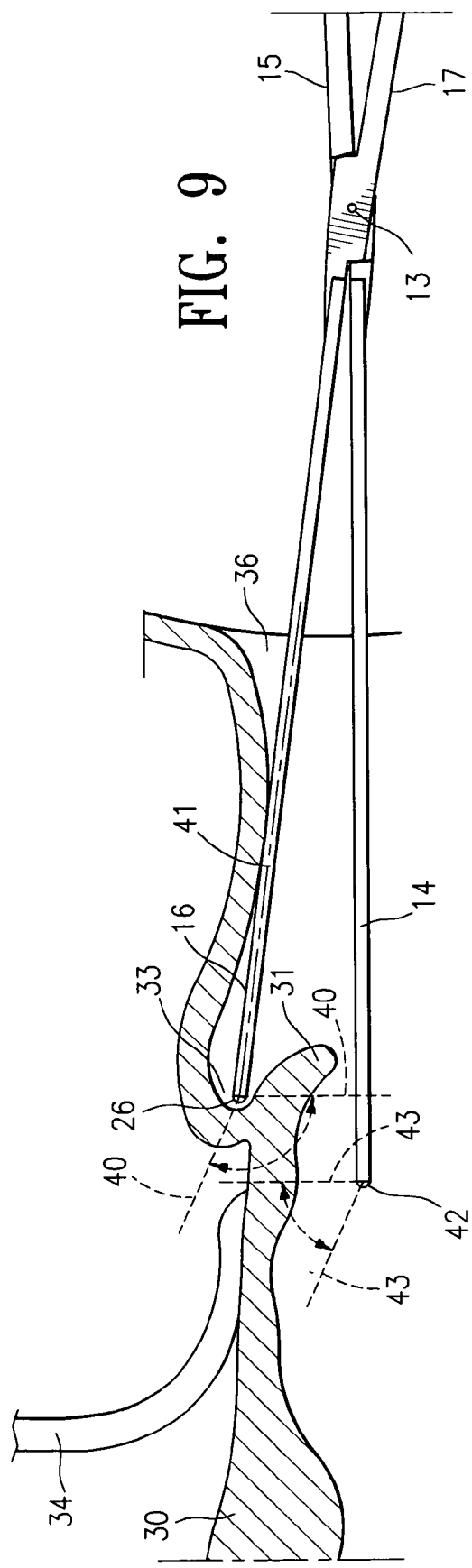
FIG. 8
FIG. 9

TREATMENT FOR POST PARTUM HEMORRHAGE

FIELD OF THE INVENTION

The invention relates generally to the field of devices and treatments of diseases and conditions by the regulation of blood flow in blood vessels. In particular, the invention is directed to the treatment of post partum hemorrhage by reducing or terminating blood flow to a female patient's uterus after giving birth.

BACKGROUND OF THE INVENTION

Some women bleed to death following childbirth. If the blood supply to the uterus can be controlled soon after birth, such deaths can be prevented. The blood supply to the uterus is predominantly from the right and left uterine arteries. In most women, the origin of each uterine artery is from the anterior division of the internal iliac artery. The uterine arteries reach the uterus traveling in the retroperitoneum and broad ligament and inserting into the uterus at the junction of the cervix of the uterus with the body of the uterus in a region of the uterus referred to as the "isthmus". The right uterine artery meets the uterus along its right lateral border at about the "9:00 o'clock" position; the left, at about the "3:00 o'clock" position. As the uterine arteries approach the uterus, they are sufficiently close to the lateral vaginal fornix (typically about 12 cm) to be touched during a bimanual pelvic examination and their pulsations can frequently be felt manually in early pregnancy.

As pregnancy advances, the uterus changes shape, increasing in volume to accommodate the growing fetus and placenta. As a result, the uterine arteries move away from the uterine introitus. The uterine arteries are fixed in two locations: the first is where they exit the retroperitoneum and enter the broad ligament and the second is where they insert into the uterus. In between these two fixed points, the uterine arteries course back and forth in the broad ligament, in a plurality of undulations over a distance of several centimeters, the undulations are only loosely attached to the broad ligament, and are surrounded by delicate fatty tissue.

As the uterus increases in volume during pregnancy, it expands out of the pelvis into the abdomen. Because the uterine arteries are fixed to the uterus, they are pulled upwards along with the growing uterus. In the process, the undulations of the uterine arteries in the broad ligament straighten. However, with the expansion of the uterus into the abdomen as the pregnancy term lengthens, the uterine arteries can no longer be palpated during a bimanual pelvic examination because they are too far away from the vaginal introitus to be reached by an examiner's fingers (typically about 19 cm). From the beginning of pregnancy to just after delivery, the insertion of the uterine arteries into the uterus typically move about 7 cm away from the vaginal introitus.

Two major events occur at birth; a baby is born and a placenta separates from the uterus. Although the birth of a baby is an immense physiological, mechanical, psychological, and social experience—except for the rare birth canal laceration—it is an insignificant vascular event.

Separation of the placenta, however, is a monumental vascular event. The approximately 100 uteroplacenta arteries that supply the placenta are radial arteries transformed and enlarged by placental trophoblast cells to the shape of trumpets at their insertion into the placenta base. As a result of their unusual shape, they deliver blood to the placenta at low velocity and high pressure. At the time of delivery, cardiac output is 6-7 L/min with blood flow through the uterus at 0.5-1.0 L/min. When the placenta separates from the uterus, the uteroplacental arteries trumpet a large volume of blood directly into the uterine cavity. Left unchecked, every woman would bleed to death within minutes. However, the vast majority of women do not because, during the nine months leading up to delivery, clotting and fibrinolytic proteins, and their control systems, increase in concentration in mother's blood. Following placental separation from the uterine wall, blood flow is slowed in the uterus by persistent, regular myometrial contractions. With increased clotting proteins present and blood flow slowed by uterine contractions, myometrial arteries clot. Shortly thereafter, clot in the uterus lyses and myometrium is reperfused. However, clot is not lysed in uteroplacental arteries. They scar and are never used again. After clot forms throughout the body of the uterus, placental tissue dies and over weeks is sloughed into the uterine cavity.

Although uterine contractions following birth are generally sufficient to slow the velocity of blood flowing through the uterus to initiate blood clot formation throughout myometrium, in some women uterine contractions are inadequate. In the postpartum hemorrhage literature, a uterus that does not contract is considered to be "atonic" and the patient is said to be suffering from "atony." Without a mechanism to slow or stop the flow of blood through the uterus, women with atony would bleed to death following childbirth.

Currently, there is a hierarchy of medical and surgical post partum interventions designed to slow the flow of blood through the uterus and help initiate uterine clot. Manual stimulation of the uterus ("uterine massage") may start uterine contractions and increase uterine tone. If uterine massage is ineffective, usually oxytocin, a hormone that helps the uterus contract, may be delivered intravenously to stimulate the uterus to contract. If oxytocin fails, ergot alkaloids and prostaglandins frequently can be administered to chemically stimulate uterine contraction. However, these pharmaceutical agents produce side effects on the vasculature not just in the uterus but throughout the body. Consequently, they are contraindicated in patients with hypertension, hypotension, toxemia, and other disease states, the very women that need postpartum hemorrhage control.

If the medical post partum managements fail, surgical interventions follow. The simplest form of surgical intervention is packing the uterus with towels and the like in an attempt to compress the bleeding placental bed sinuses and arteries to initiate clotting. If the uterine packing fails, more complex surgery is performed. One surgical technique includes performing a laparotomy and then encircling the uterus with gross sutures and compressing the uterus by cinching the sutures tight.

Other types and configurations of gross sutures have been applied to the uterus during laparotomy to compress myometrium to try to arrest postpartum bleeding. In an attempt avoid compressing myometrium with gross sutures, it has been proposed to compress branches of the uterine arteries, themselves by blindly clamping two standard ring forceps to each lateral vaginal fornix in an effort to stop the hemorrhage. Though noninvasive, this method has no means for positively identifying whether or nor any artery has been compressed by the two sets of forceps. As a result, the method has not been adopted.

To slow the flow of blood in the uterine arteries in a variety of clinical situations, bilateral internal iliac artery ligation has been performed since the late nineteenth century. However, because vascular surgery is not generally taught in obstetric residencies, the technique is not widely practiced. However, some have ligated the internal iliac arteries to slow blood flow to the uterus to treat postpartum hemorrhage. Though effective, these techniques are not universally available and there is considerable time delay between the onset of postpartum hemorrhage and the transfer to an angiographic suite—commonly in different parts of the same hospital. Furthermore, since angiography is performed by radiologists and babies are delivered by obstetricians, communication gaps arise between the two specialties. Though at times effective, the internal iliac arteries supply the whole pelvis, not just the uterus. Their occlusion, therefore, stops blood flow to more than just the uterus. Furthermore, because of complex external iliac artery to internal iliac artery anastomoses, occlusion of the internal iliac artery only lowers pressure in the uterine arteries, it does not completely stop flow in the uterine arteries. Recognizing these limitations, open, transperitoneal surgical ligation of the uterine arteries, and laparoscopic uterine artery occlusion have been developed to treat postpartum hemorrhage.

Ligation of the uterine arteries is effective at stopping postpartum hemorrhage, but the procedure is invasive and time consuming. Uterine artery occlusion is generally performed emergently, when loss of time may equate with loss of life. To reduce the operative time and the surgical skill requirements that accompany selective ligation of the uterine arteries, bilateral arterial "bulk" ligation has been performed on the ascending branch of the uterine artery. In a bulk ligation the area of the ascending uterine artery is bundled together with adjacent myometrium and ligated. A bulk ligation requires a surgical laparotomy.

Angiographic catheter-based occlusive methods directed by fluoroscopy have been developed to treat postpartum hemorrhage by stopping blood flow in the arteries that feed the uterus. However, because the angiographic methods are performed by different specialists at different locations, there is frequently insufficient time to perform them for effective treatment of PPH.

Frequently, as in the past, many surgeons today stop postpartum hemorrhage by performing a hysterectomy which is a major operation with significant morbidity and mortality. Moreover, the procedure leaves the mother infertile.

Accordingly, there is need for uncomplicated instruments that can be rapidly deployed to partially or completely terminate blood flow in blood vessels such as the uterine arteries, particularly in the case of PPH.

SUMMARY OF THE INVENTION

The invention is directed to instruments and the use of the instruments for accessing a blood vessel and occluding blood flow in the accessed blood vessel to reduce or eliminate hemorrhaging. The invention is particularly directed to the occluding of uterine arteries in the treatment of PPH following vaginal delivery.

A blood vessel occlusion instrument having features of the invention is a clamping device having a pair of pivotally connected clamping members with each of the clamping members having an elongated handle with an operative distal end and a manipulative proximal end and a clamping element at the operative distal end of the handle. The clamping elements are inclined with respect to the longitudinal axis of the handle to which they are joined with an included obtuse angle of about 120° to about 170°, preferably about 130° to about 160° to facilitate placement. The clamping members are pivotally connected so that rotation of the handles about the pivot point opens and closes the clamping elements.

One of the clamping elements of the clamping device is preferably larger than the other clamping element so that the smaller clamping element at least partially fits inside the larger clamping element when the clamping elements are brought together, i.e. when the clamping device is closed or partially closed. The larger clamping element may be longer or wider or both longer and wider than the smaller clamping element. At least one of the clamping members, preferably the outer and smaller clamping element, is provided with at least one blood vessel location sensor at or near the distal end of the clamping element. The sensors are mounted on the distal end of the clamping element to facilitate location of the target uterine artery when positioned adjacent thereto. The at least one sensor has a field of view which radiates distally from the distal end of the clamping element to which it is mounted to facilitate location and occlusion of the patient's uterine artery. One or more sensors may be mounted on the clamping elements having a field of view toward an opposing clamping element to aid in monitoring blood flow through an occluded or partially occluded artery compressed by one or both clamping elements.

The clamping device embodying features of the invention is configured to be inserted into a female patient's vaginal canal and advanced therein after a vaginal birth. The first or inner clamping element is disposed within the patient's uterine cervix and the second or outer clamping member disposed on the outside of the patient's uterine cervix. The inclination of the clamping elements with respect to the longitudinal axis of the handles helps with the proper placement of the clamping elements within the patient's post partum anatomy.

The handles of the clamping device may be provided with a locking mechanism to provide the clamping device with a releasable clamped configuration effective to retain the clamping elements in a pressure-applying configuration. The pressure applying surfaces of the clamping elements are preferably provided with surface characteristics such as serrations or knurling to ensure a good grip on tissue when the clamping elements are closed about tissue received within the clamping elements.

A location sensor for locating a blood vessel is disposed in or on the distal ends of one or both clamping elements. The location sensor may be a blood flow sensor, such as a Doppler ultrasound sensor, and may be configured to operate with a sensor controller configured to provide a signal related to the sensor output, such as an audible signal, that may be readily interpreted or used by an operator.

The invention provides a method of treating a patient suffering from PPH which includes locating the uterine artery with a location sensor on the distal end of a clamping element of the clamping device having features of the invention, and compressing a portion of the uterine artery by applying pressure to tissue with the clamping elements of the clamping device. To properly deploy the device, the inner clamping element is placed within a uterus of a patient and the outer clamping element is disposed about a portion of the uterine cervix near the adjacent vaginal fornix of a patient. The clamping device is pushed further into the patient's vaginal canal so the distal end of the outer clamping element distends the wall of the patient's vaginal fornix near to the patient's uterine artery so the outer clamping element folds the vaginal wall over the uterine artery. Closing of the clamping device compresses the uterine artery to effectively reduce or abolish blood flow in the uterine artery. Compression of the uterine artery may be maintained from several minutes up to several hours in order to reduce or terminate the post partum hemorrhage and to effect sufficient clotting so as to reduce the risk of further hemorrhage upon release of the clamping device from its closed or partially closed condition. Thus, compression may be maintained for a therapeutically effective amount of time, typically between about 5 minutes and about 7 hours, preferably about 10 minutes to about 5 hours.

The invention enables non-invasive identification and occlusion of blood vessels such as the uterine arteries to treat PPH. The devices and methods are simple and easy to use, enabling the rapid and effective occlusion of a female patient's uterine arteries after giving birth without surgical intervention.

BRIEF DESCRIPTION OF THE DRAWINGS

FIG. 2 is an elevational view of the clamping device shown in FIG. 1.

FIG. 3 is an elevational view of the clamping device shown in FIG. 1 taken at 90° from the view shown in FIG. 2.

FIG. 4 is a transverse cross sectional view of the clamping members 14 and 16 taken along the lines 4-4 shown in FIG. 2.

FIG. 8 is a partial cross-sectional view taken along the lines 8-8 shown in FIG. 7 with a clamping device embodying features of the invention deployed to occlude the uterine artery.

FIG. 9 is an enlarged elevational view partially in section illustrating the clamping elements in a partially clamped configuration to occlude the patient's uterine artery.

DETAILED DESCRIPTION OF THE INVENTION

Figure 1:
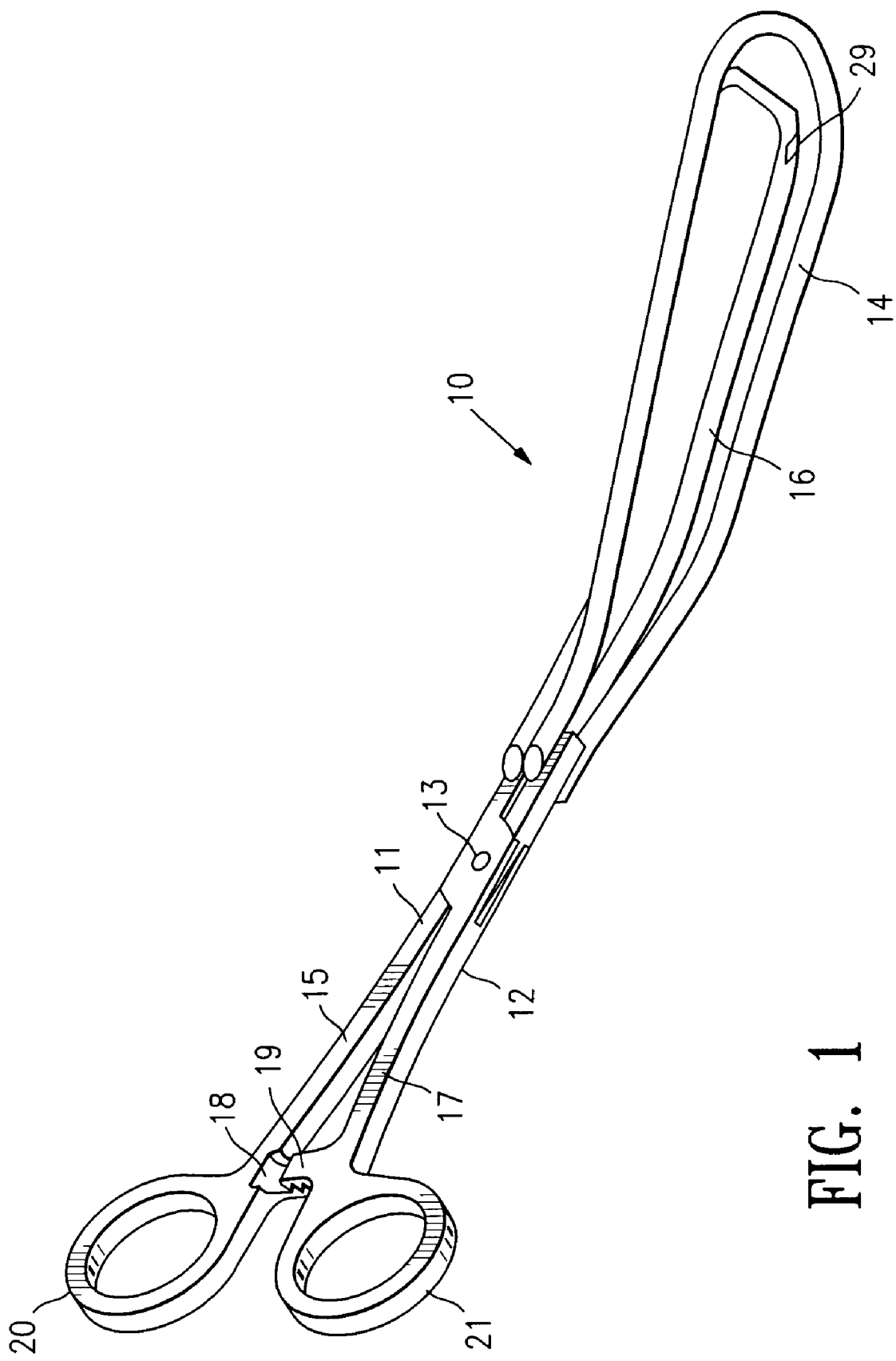
FIG. 1 is a perspective view of a clamping device embodying features of the invention.

FIGS. 1-5 illustrate a clamping device 10 embodying features of the invention including first and second clamping members 11 and 12 which are pivotally connected at pivot point 13. First clamping member 11 has a first clamping element 14 secured to the distal end of handle 15. Second clamping member 12 has a second clamping element 16 secured to the distal end of handle 17. The handles 15 and 17 are provided with ratchet members 18 and 19 respectively to provide a releasable locking connection therebetween and finger grips 20 and 21 respectively for rotating the handles about the pivot point 13 to open and close the clamping elements 14 and 16. Each of the clamping elements 14 and 16 are at angles with respect to the longitudinal axis of the handles 15 and 17 to facilitate deployment within the patient's post partum vaginal canal and uterine cervix. The clamping elements 14 and 16 form an obtuse included angle θ with respect to the longitudinal axis of handles 15 and 17 so as to be advanced through the patient's vaginal canal and allow the ready disposition of one of the clamping elements within the patient's cervix and the other clamping element on the outside of a uterine cervix. The included obtuse angle θ between the clamping elements 14 and 16 and the handles 15 and 17 respectively is about 120° to about 170°, preferably about 130° to about 160°. Preferably, both included angles should be essentially the same.

As best shown in FIG. 2, the clamping element 16 is smaller than clamping element 14 and preferably is configured so the outer perimeter of distal portion 22 of clamping element 16 is smaller than the inner perimeter of the distal portion 23 of clamping element 14 as shown. The larger clamping element 14 is designed to be disposed within the patient's uterine cervix and the smaller clamping element 16 is designed to be disposed on the exterior of the uterine cervix. The clamping elements 14 and 16 have inner pressure-applying surfaces 24 and 25 respectively which are preferably serrated or knurled (not shown) to provide a good tissue grip when the clamping device is in a closed configuration. Each of the clamping elements generally lies in a plane which is perpendicular to the plane in which the handles rotate.

The clamping elements 14 and 16 are sized and configured so that they can cooperate to compress a uterine artery after the patient has given birth. They may have lengths of about 0.8 inch to about 6 inches (mm-mm), and preferably between about 2.5 inches and about 5 inches (mm-mm). The widths of the clamping elements 14 and 16 are about 0.5 inch to about 3 inches (12.7 mm-76.2 mm), preferably about 0.7 inches. to about 1.5 inch (17.8 mm-38.1 mm), and more preferably about 0.8 inch (20.3 mm). Additionally, the transverse dimensions of the clamping elements 14 and 16 ranges from about 0.07 inch to about 0.2 inch (1.78 mm-5.1 mm), preferably about 0.12 inch to about 0.16 inch (3.1 mm-4.1 mm). Typically, the diameter of the wire frame is preferably about 0.14 inch (mm). The clamping element 14 is preferably is longer then the clamping element 16 by a distance "d", which may range from about 0.1 to about 1 inch (2.54 mm 25.4 mm), preferably about 0.1 to about 0.3 inch (2.54 mm-7.6 mm). The open, wire-frame nature of the clamping elements 14 and 16 are illustrated in FIG. 4.

The handles 15 and 17 of the clamping device 10 have lengths of about 3 to about 10 inches (7.62 cm-25.4 cm) to allow an operator to grasp the finger grips 20 and 21 on the proximal ends of the handles while advancing the clamping members within a patient's vagina, until the inner clamping element is within the patient's uterine cervix and the outer clamping element is adjacent to a vaginal fornix of a female patient. Handles 15 and 17 are configured for manipulation by an operator to rotate the handles by manipulation of the fingers engaged within finger grips 20 and 21 in a plane about pivot point 13, transmitting the force applied by the operator in a desired direction to open or close the clamping elements 14 and 16 secured thereto.

Figure 5:
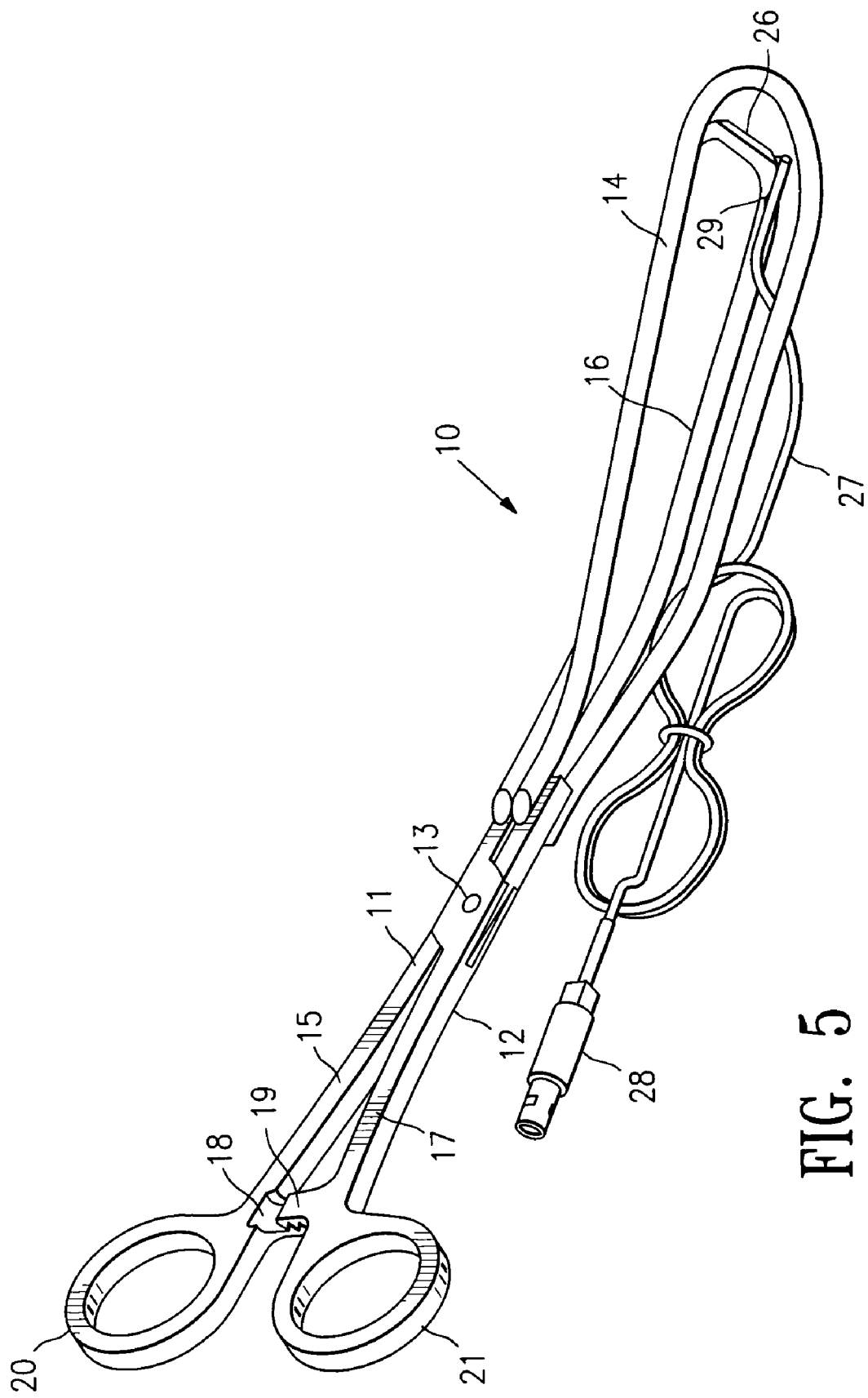
FIG. 5 is a perspective view of a system including the clamping device shown in FIG. 1, having a blood vessel locating sensor and a signal transmitting member associated with the sensor.

In FIG. 5, the clamping device 10 shown in FIGS. 1-3 is provided with a blood vessel location sensor 26 that is mounted on a distal end of clamping element 16. A signal transmitting electrical conductor 27 is connected by its distal end to the sensor 26 and has an electrical connector 28 on its proximal end suitable to be connected to a sensor controller (not shown). As better shown in FIG. 2, clamping element 16 is provided with a slot 29 to accommodate the electrical conductor 27.

As previously mentioned, at least the outer clamping element 16 has a location or blood flow sensor 26 and, as shown in FIG. 5, the location sensor 26 is located at the distal tip of the outside clamping element 16. Additional locations are possible. A location sensor 26 (or location sensors 18) is disposed on clamping element positioned effective to detect blood flow in a blood vessel when the clamping element is near to or in contact with tissue containing the target artery. The sensor 26 is preferable oriented to view forward of the leading edge of the clamping element 16, so that forward motion of the clamping device will push the sensor closer to the target artery and better pin point the location of the artery.

Figure 7:
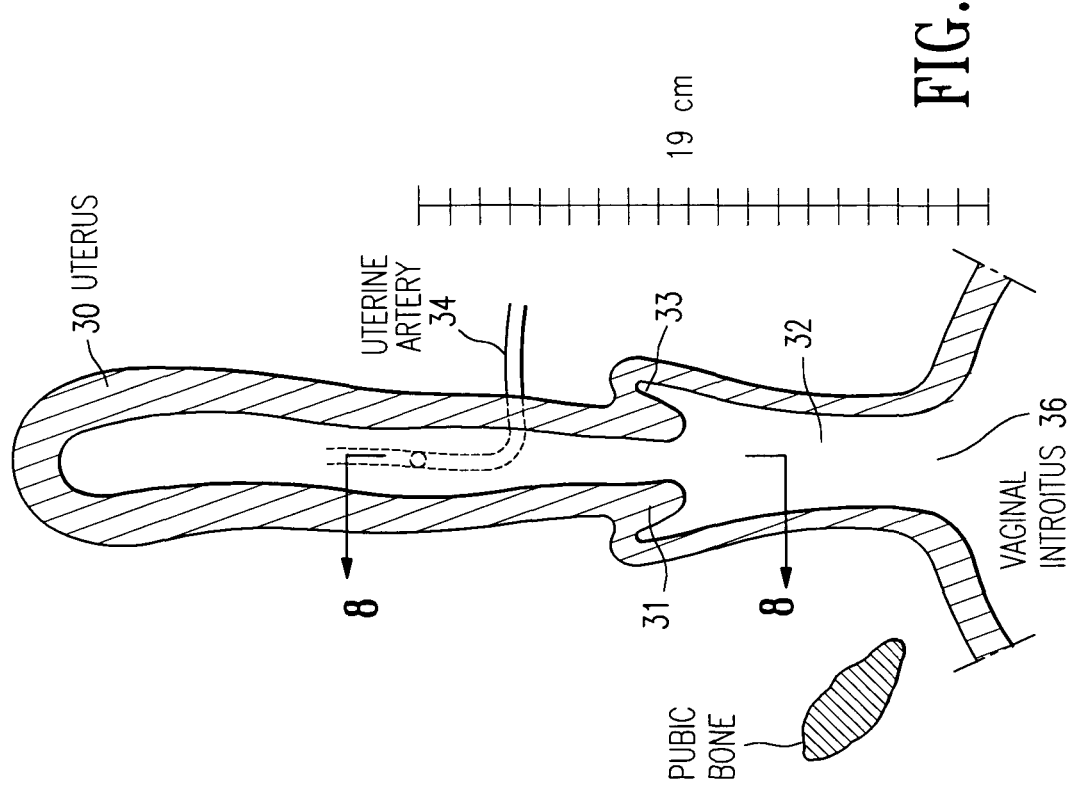
FIG. 7 is a sagittal view of a female patient's vagina and uterus shortly after giving birth illustrating the anatomical changes which have occurred when compared to FIG. 6.
Figure 6:
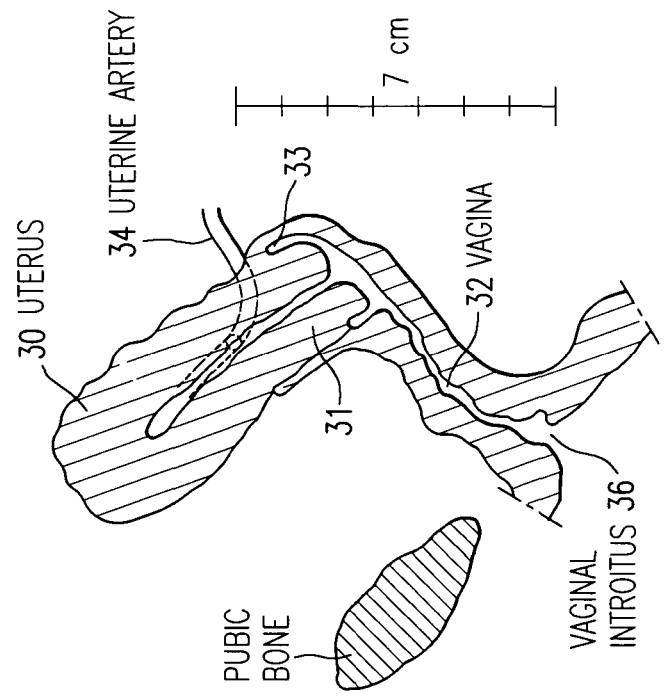
FIG. 6 is a sagittal view of a female patient's vagina and uterus in early pregnancy.

FIG. 6 illustrates female anatomy early in a patient's pregnancy. Depicted are the uterus 30, the uterine cervix 31 and vaginal canal 32, the vaginal fornix 33, the uterine arteries 34 and 35 and the vaginal introitus 36. As the pregnancy progresses, the uterus 30 expands into the patient's abdominal area to accommodate the growing fetus. As discussed in the Background, this growth results in the uterine arteries 34 and 35 extending much farther away from the patient's vaginal fornix, e.g. 7 cm from the vaginal introitus 36 early in the pregnancy to 19 cm or more at the full term termination of the pregnancy. FIG. 7 illustrates the same female anatomy after a full term vaginal delivery. As shown, after delivery, the cervix 31 is typically radially expanded to a much larger diameter and elongated, the uterine arteries 34 and 35 are much further away from the vaginal fornix 33 and the vaginal introitus 36, as compared to early in the pregnancy.

FIG. 8 depicts a clamping device 10 disposed within the patient's after delivery anatomy in a front view, partially in section, to the view shown in FIG. 7. As shown, clamping element 14 extends through the uterine cervix 31 and clamping element 16 is disposed on the exterior of the uterine cervix with the distal end thereof pressing against the vaginal fornix 33 to fold the fornix over the uterine artery 34. When the physician closes the handles 15 and 17 of the clamping device 10, clamping elements 14 and 16 compress the tissue disposed therebetween and occlude the uterine artery 34 which underlies the vaginal fornix 33. The handles 15 and 17 are pressed together to interlock the ratchet elements 18 and 19 to lock the clamping elements 14 and 16 in a closed configuration. After one uterine artery is occluded, or during the occlusion of the first uterine artery, a second clamping device similar to the first clamping device may be deployed in a similar fashion on the other side of the patient's anatomy to occlude the other uterine artery 35. Effective treatment of PPH usually requires occlusion of both the right and the left uterine arteries. After a suitable time, the clamping devices 10 are released and, if the hemorrhaging has ceased or is at least under control, the clamping devices may be removed from the patient. For effective treatment of PPH, the clamping devices may be locked in a closed configuration for a few minutes up to several hours, but typically less than 24 hours. For example, uterine artery occlusion lasting for between about 5 minutes and up to about 7 hours, preferably between about 10 minutes and about 5 hours, may be sufficient to treat PPH.

The clamping device 10 shown in FIG. 8 was not depicted with an artery location sensor 26 as shown in FIG. 5 in order to simplify the drawing. FIG. 9 is an enlarged schematic view of the distal end of clamping elements 14 and 16 clamped against the exterior of a female patient's post partum cervix 31. In this drawing, artery sensor 26 is mounted on the leading surface of the distal end of clamping element 16. The field of view of the sensor 26 is schematically illustrated in two dimensions by the dotted lines 40. In reality, the field of view is cone shaped. The direction of the field of view is along the longitudinal axis 41 of clamping element 16 to enable detecting the location of uterine artery 34. The sensor 26 is preferably oriented to view forward of the leading edge of the clamping element 16, so that forward motion of the clamping device will push the sensor 26 closer to the target uterine artery 34 and better pin point the location of the artery. Additionally, another sensor 42 may have a field of view illustrated by the dotted lines 43 from the clamping element 14 toward the clamping element 16 through the tissue therebetween. The sensor 26 may be employed to both locate the uterine artery 34 and to monitor its occlusion upon closing the clamping elements 14 and 16 against the tissue of the vaginal fornix 33.

Figure 10:
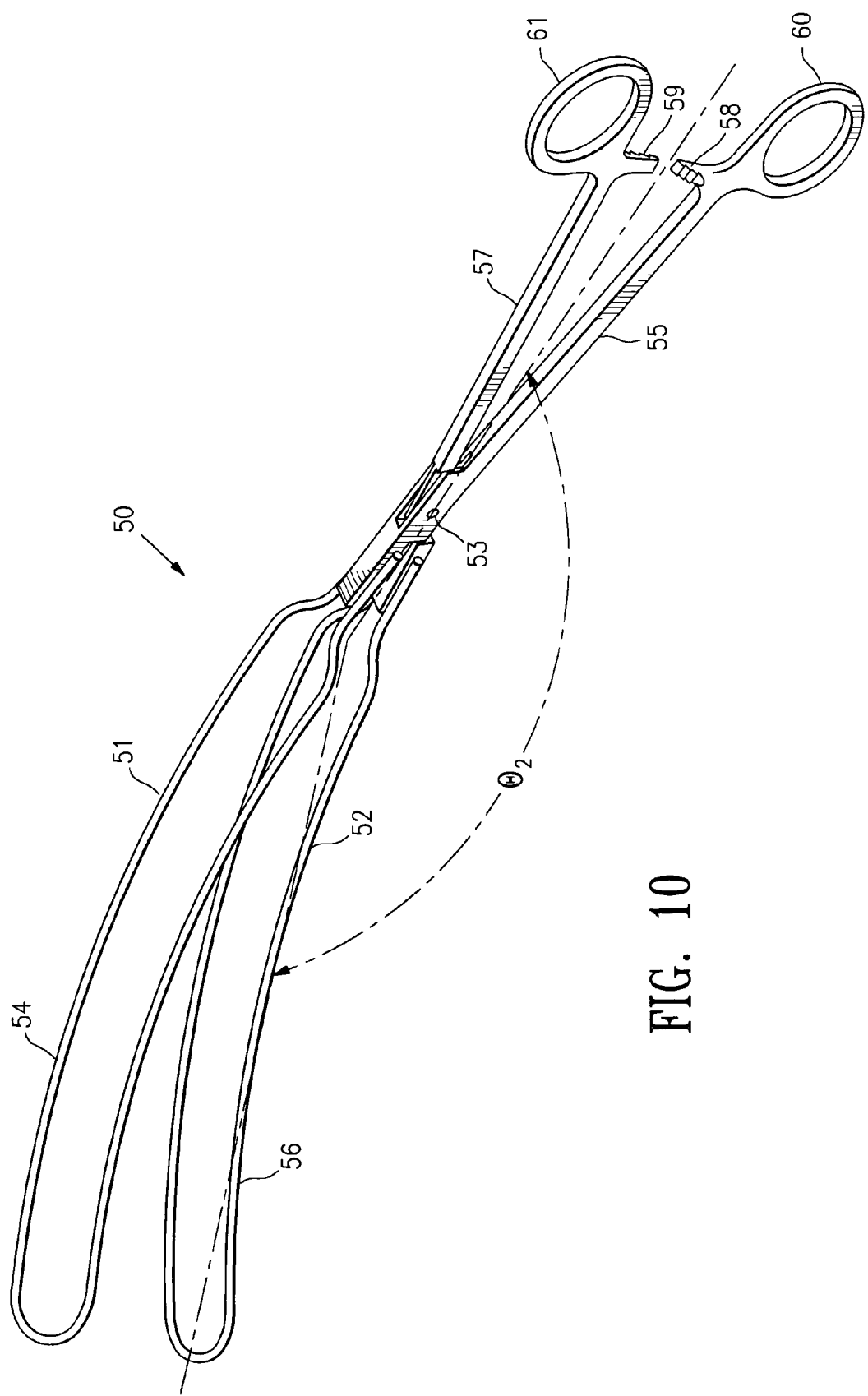
FIG. 10 is a perspective view of an alternative embodiment of a clamping device wherein the clamping elements of the device are curved.
Figure 11:
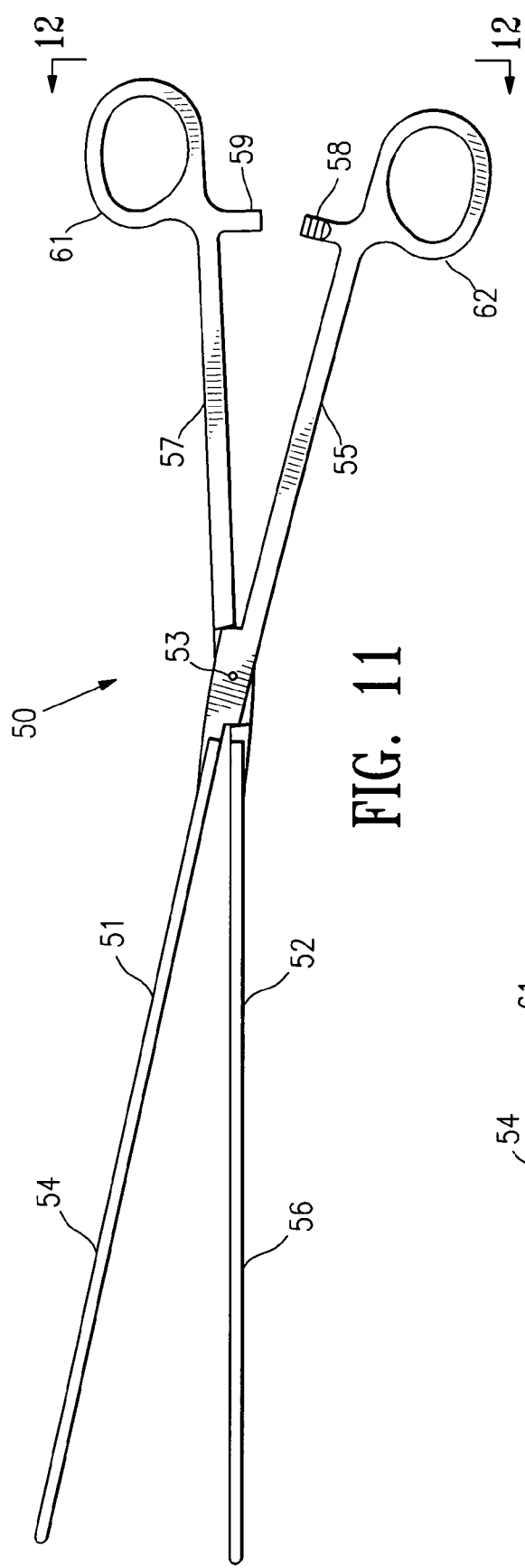
FIG. 11 is an elevational view of the clamping device shown in FIG. 10 in an open configuration.
Figure 12:
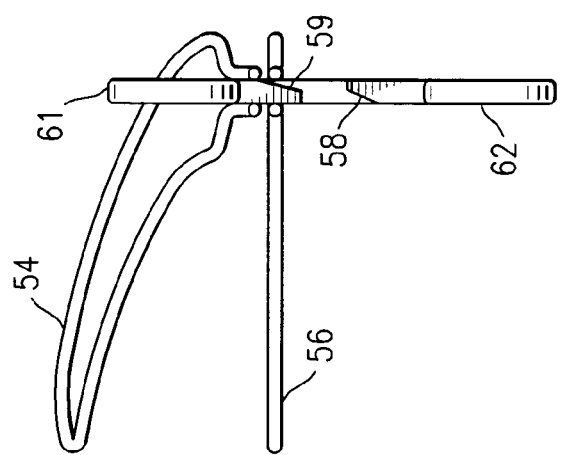
FIG. 12 is an end view of the device shown in FIG. 10.

FIGS. 10-12 illustrate an alternative embodiment of a clamping device 50 embodying features of the invention. The clamping device 50 includes first and second clamping members 51 and 52 which are pivotally connected at pivot point 53. First clamping member 51 has a first curved clamping element 54 secured to the distal end of handle 55. Second clamping member 52 has a second curved clamping element 56 secured to the distal end of handle 57. The handles 55 and 57 are provided with ratchet members 58 and 59 respectively to provide a releasable locking connection therebetween and finger grips 60 and 61 respectively allow for manual rotation of the handles 55 and 57 to open and close the clamping elements 54 and 65. Each of the clamping elements 54 and 56 are curved away from the longitudinal axis of the handles 55 and 57 to facilitate deployment within the patient's vaginal canal and uterine cervix and they lie in a plane generally perpendicular with respect to the plane in which the handles 55 and 57 are rotated. A line 62 drawn through the ends of the curved clamping elements 54 and 56 generally forms an obtuse included angle θ with respect to the longitudinal axis of the handle in a similar fashion as the clamping elements 14 and 16 shown in FIGS. 1-4 so as to be easily advanced through the patient's vaginal canal and allow the ready disposition of one of the clamping elements within the patient's post partum cervix and the other clamping element on the outside of a post partum uterine cervix. The dimensions of the clamping device 50 depicted in FIGS. 10-12 are essentially the same as those of the embodiment shown in FIGS. 1-4. Blood flow sensors may be provided on the distal end of at least the outer clamping element 54 as shown in FIG. 4.

While the clamping devices described herein have clamping members in which the clamping element and the handle are integrally formed, alternative embodiments may include clamping elements that are releasably secured to the handles such as the embodiments shown in co-pending application Ser. No. 10/300,116, filed on Nov. 19, 2002, entitled "OCCLUSION DEVICE WITH DEPLOYABLE PADDLES FOR DETECTION AND OCCLUSION OF BLOOD VESSELS" (Burbank et al.), which is incorporated herein in its entirety by reference.

Figure 14:
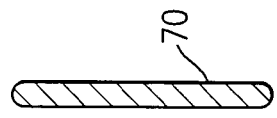
FIG. 14 is a cross-sectional view taken along line 14-14 shown in FIG. 12.
Figure 16:
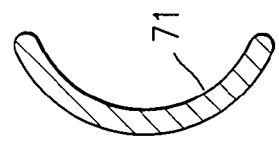
FIG. 16 is a cross-sectional view taken along line 16-16 shown in FIG. 14.
Figure 13:
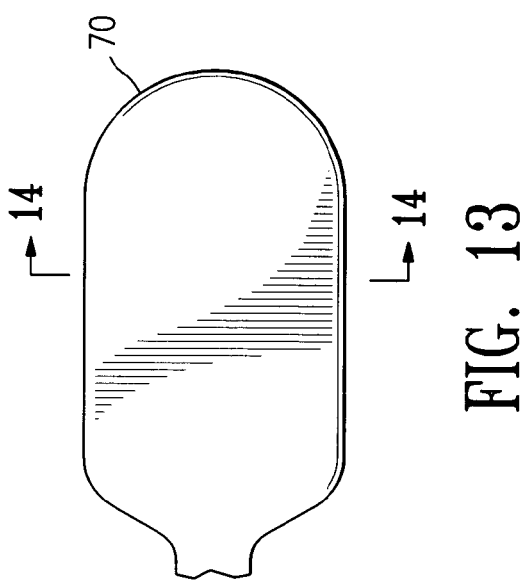
FIG. 13 is a top plan view of a planar solid clamping element having features of the invention.
Figure 15:
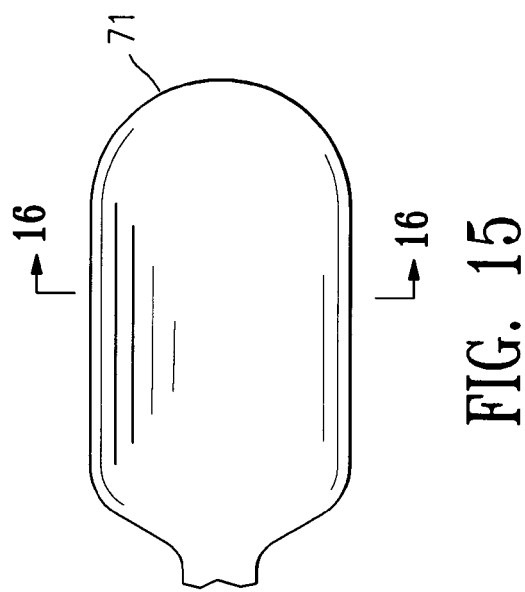
FIG. 15 is a top plan view of a curved solid clamping element having features of the invention.

The clamping elements 14 and 16 are shown in FIGS. 1-4 and clamping elements 54 and 56 are shown in FIGS. 10-12 as open, paddle-like wire frames. However, the clamping elements may be solid, paddle-like element 70 and 71 as shown in FIGS. 13-16. As shown in FIGS. 13-14, the paddle-like clamping element 70 is a flat solid member, whereas in FIGS. 15-16 the paddle-like clamping element 71 has a curved semi-cylindrical structure. The curved paddle-like clamping element 71 shown in FIGS. 15 and 16 is preferably configured to approximate the curved inner or outer surface of the patient's cervix. The opposing curved clamping elements (not shown) are preferably configured with similar and complementary curvatures so as to fit together and to compress the patient's cervical wall.

An effective amount of pressure, suitable for occluding a blood vessel by compressing a blood vessel or tissue adjacent a blood vessel with the clamping elements of the present invention, is typically between about 3 pounds per square inch (psi) and about 200 psi, preferably between about 3 psi and about 80 psi, more preferably between about 5 psi and about 30 psi.

The location or blood flow sensor such as sensor 26 may be a suitable sensor for locating a blood vessel and including a sensor configured for detecting blood flow. The sensor may be passive (i.e. detecting intrinsic signals indicating the presence of a blood vessel) or active (producing a signal and detecting a response to it). Suitable sensors include sound location sensors (e.g., a microphone capable of sensing blood flow sounds), ultrasound sensors, a pressure sensor, stress or strain sensor for detecting pulsations in a blood vessel due to heart action, an electromagnetic location sensor (e.g., infrared location sensor) to detect a blood vessel (e.g., to detect hemoglobin), a pH or other chemical location sensor, or other location sensor.

Ultrasound reflected by moving blood cells within a patient's artery undergoes a frequency shift. Ultrasound reflected back from blood cells moving away from the ultrasound source in an artery has a lower frequency than the source ultrasound frequency; ultrasound reflected back from blood cells moving towards the source has a higher frequency than the source frequency. This Doppler frequency shift phenomenon can be measured by transceiver electronics and sent to a speaker to create sounds detectable by an operator or to a display device or monitor. For example, a change in blood velocity may be signaled by a change in the frequency (i.e., pitch) of the loudspeaker output signal, or by the volume of the loudspeaker output signal.

Preferably, the location sensor 26 is a Doppler ultrasound sensor, configured to emit and to detect ultrasound signals effective to locate the patient's uterine artery and to detect the blood flow therethrough. Doppler ultrasound systems typically include a sensor controller (not shown) that may include an electrical connector 28 to plug in the location sensor, a power switch to power-on the transceiver electronics, an audible speaker output so that an operator can hear the Doppler frequency shift, a volume adjustment to control overall sound level, and batteries or other power source to provide energy. Location sensor 26 may be operably connected to a sensor controller (not shown) by a sensor cable such as conductor 27 shown in FIG. 5. A sensor controller is preferably configured to receive information from the sensor and may also provide power to the sensor, may serve as a signal source, a signal output (e.g., may provide an audible sound related to the location sensor output) and may control the operation of the sensor.

In use, a sensor controller (not shown) is typically situated outside a patient's body and connected to sensor 26 disposed on or within a patient's body. A sensor controller may connect with a single sensor, or with multiple sensors. Commercially available Doppler ultrasound sensors and sensor systems suitable for use in the present invention include the Koven model ES 100X MiniDop VRP-8 probe (St. Louis, Mo.), the DWL/ Neuro Scan Medical Systems' Multi-Dop B+ system (Sterling, Va.), and the MedaSonics® CardioBeat®) Blood Flow Doppler with Integrated Speaker (Cooper Surgical, Inc., Trumbull Conn. 06611)). To detect blood flow in the uterine arteries with ultrasound transducers, the ultrasound transducers should point axially into the patient's tissue and insonate it up to a depth of approximately 3 cm or more (attenuated through tissue) for 8 MHz systems. As previously described, the bilateral uterine arteries run laterally inward from sidewall of pelvis to the uterus just behind the vaginal mucosa near the cervix, and are by far the single largest blood vessels in this area, making their detection by ultrasound relatively straightforward. In addition, a Doppler crystal may be optimized for uterine vessel detection by configuring it to detect blood flow in a wide region detected by the location sensors. The frequency of the ultrasound energy used for Doppler ultrasound will change the viewing angle of the ultrasound system. Use of Doppler crystals as both a location sensor and as an ultrasound source permits Doppler data to be gathered at distances up to about 3 cm from the source. When a clamping element on which a Doppler crystal is mounted is pushed against a uterine wall, a cervical wall, or against tissue adjacent the vaginal fornix, the Doppler crystals will receive reflected signals from the uterine artery of interest. Thus, while many different Doppler crystals are suitable in the present invention, those which operate at frequencies between about 5 MHz and 20 MHz, preferably between about 6 MHz and about 10 MHz, more preferably at a frequency of about 8 MHz have been found to be particularly suitable.

A location sensor may also be, for example, an infrared or other electromagnetic location sensor. Electromagnetic energy useful for sensing a location of a blood vessel or of blood flow in a blood vessel may have a wavelength of between about 500 nanometers (nm) and about 2000 nm, preferably between about 700 nm and about 1000 nm.

The present invention is particularly effective when used in the treatment of excessive bleeding after vaginal delivery commonly referred to as PPH. Accordingly, when it is recognized that bleeding has not stopped normally as it should after delivery, devices and/or methods in accordance with the present invention can be deployed as described herein to slow or stop PPH.

Blood vessel-occluding devices embodying features of the invention may be made from any suitable material or combination of materials, including metals such as stainless steel and shape memory alloys such as nickel titanium alloys, other biocompatible and preferably sterilizable metals, plastics, ceramics, and other materials known in the art. Biocompatible polymers, preferably sterilizable thermoplastic and thermoset materials such as for example, polycarbonate, polysulfone, polyester, polyethylene, polyacetal, and other polymers may be particularly suitable for embodiments of the invention. It will be understood that devices and systems may comprise any one or combinations of these and similar materials. The device or system may be designed for single use (disposable) or may be sterilizable and capable of being used multiple times.

While particular forms of the invention have been illustrated and described, it will be apparent that various modifications can be made without departing from the spirit and scope of the invention. Accordingly, it is not intended that the invention be limited to the specific embodiments illustrated. It is therefore intended that this invention to be defined by the scope of the appended claims as broadly as the prior art will permit, and in view of the specification if need be. Moreover, those skilled in the art will recognize that features shown in one embodiment may be utilized in other embodiments. Terms such a "element", "member", "device", "sections", "portion", "section", "steps" and words of similar import when used herein shall not be construed as invoking the provisions of 35 U.S.C. §112(6) unless the following claims expressly use the terms "means" or "step" followed by a particular function without specific structure or action. All patents and patent applications referred to above are hereby incorporated by reference in their entirety.

What is claimed is:

1. A method of treating a female patient suffering from PPH, comprising:
   a. providing an intravaginal clamping device having
      i. a first clamping member which has an elongated handle with a distal operative end and a proximal manipulative end and a clamping element secured to the operative distal end at an obtuse angle with respect to the first handle;
      ii. a second clamping member which has a second elongated handle with a distal operative end and a proximal manipulative end and a second clamping element secured to the operative distal end of the second elongated handle at an obtuse angle with respect to the second elongated handle;
      iii. a pivotal connection between the first and second clamping members so that rotation of the first and second handles within a rotational plane about the pivotal connection adjusts spacing between the first and second clamping elements with the clamping elements extending out of the rotational plane of the first and second handles; and
      iv. a blood flow sensor on a pressure applying surface on the distal end of the second clamping element;
   b. introducing the intravaginal clamping device into the patient's vaginal canal, and advancing the device therein until the first clamping element of the device is disposed within the patient's uterine cervix and the second clamping element of the device is disposed on the exterior of the patients uterine cervix;
   c. further advancing the device within the patient's vaginal canal to press the pressure applying surface of the second clamping element against a region of the patient's vaginal fornix to fold the tissue of the vaginal fornix over underlying uterine tissue;
   d. detecting blood flow through the patient's uterine artery to ensure that the pressure applying surface of the second clamping element is located over the patient's uterine artery; and
   e. compressing the handles of the device together to close at least the second clamping element against the patient's vaginal fornix and underlying uterine tissue to at least partially occlude the uterine artery.

2. The method of claim 1, wherein the first and second clamping members are locked in a closed configuration in which the clamping elements at least partially occlude a uterine artery of the patient.

3. The method of claim 1, wherein the blood flow sensor is a Doppler ultrasound sensor.

4. The method of claim 3, wherein the Doppler ultrasound sensor emits ultrasound toward the uterine artery having a frequency of between about 5 MHz and about 20 MHz.

5. The method of claim 3, wherein the Doppler ultrasound sensor detects a change in blood flow in the blood vessel.

6. The method of claim 5, wherein the Doppler ultrasound sensor detects a reduction in blood flow in the blood vessel.

7. The method of claim 1, wherein the clamping members apply a pressure of between about 3 psi and about 80 psi.

8. The method of claim 1, wherein the clamping members apply a pressure of between about 5 psi and about 30 psi.

9. The method of claim 1, wherein the uterine artery is at least partially occluded for a period less than 24 hours.

10. The method of claim 1, wherein the uterine artery is at least partially occluded for a period comprising between about 5 minutes and about 7 hours.

11. The method of claim 1, wherein the uterine artery is at least partially occluded for a period comprising between about 10 minutes and about 5 hours.

* * * * *